United States Patent
Scheiner

(10) Patent No.: US 8,755,889 B2
(45) Date of Patent: Jun. 17, 2014

(54) METHOD AND APPARATUS TO ENHANCE THERAPY DURING STIMULATION OF VAGUS NERVE

(75) Inventor: Avram Scheiner, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 935 days.

(21) Appl. No.: 12/771,154

(22) Filed: Apr. 30, 2010

(65) Prior Publication Data

US 2011/0270329 A1    Nov. 3, 2011

(51) Int. Cl.
*A61N 1/08* (2006.01)
(52) U.S. Cl.
USPC .................................. 607/42; 607/2
(58) Field of Classification Search
USPC .............................................. 607/42
See application file for complete search history.

(56) References Cited

U.S. PATENT DOCUMENTS

| | | | |
|---|---|---|---|
| 3,421,511 A | 1/1969 | Schwartz et al. | |
| 5,025,807 A | 6/1991 | Zabara | |
| 5,111,814 A | 5/1992 | Goldfarb | |
| 5,205,285 A | 4/1993 | Baker, Jr. | |
| 2005/0065553 A1 | 3/2005 | Ben Ezra et al. | |
| 2008/0058892 A1* | 3/2008 | Haefner et al. | 607/45 |
| 2008/0234780 A1 | 9/2008 | Smith et al. | |

OTHER PUBLICATIONS (PCT/US20100/030474) PCT Notification of Transmittal of the International Search Report and the Written Opinion of the International Searching Authority, Mailed Jul. 25, 2011, 11 pages.

* cited by examiner

*Primary Examiner* — Michael Kahelin
(74) *Attorney, Agent, or Firm* — Reed A. Duthler

(57) ABSTRACT

A method and apparatus stimulating a vagus nerve of a patient. The apparatus includes a pulse generator having an adjustable pulse output parameter and adapted to be electrically coupled to the vagus nerve. The pulse generator generates pulses for a burst period that is followed by a rest period. The apparatus also includes a respiration sensor coupled to the pulse generator. The respiration sensor detects the inspiration and the expiration phases of the respiration. The pulse generator generates stimulation pulses during both the detected inspiration and expiration phases. The pulses are delivered with the output parameter adjusted to provide greater stimulation strength during the inspiration phase than during the expiration phase.

11 Claims, 4 Drawing Sheets

METHOD AND APPARATUS TO ENHANCE THERAPY DURING STIMULATION OF VAGUS NERVE

FIELD OF THE INVENTION

This document relates generally to a medical device and more particularly to a method and apparatus to reduce side effects and enhance therapy in a vagal nerve stimulation system.

BACKGROUND

Electrical stimulation has been used for beneficial effect in medicine, most notably for cardiac pacemakers, to sustain the rhythm of the heart. The nerves of the body respond to electrical impulses. In addition to the heart, the nerves of the body have been targets for artificial electrical stimulation. Unlike cardiac stimulation in which a single pulse can trigger a contraction of the entire heart, neurological stimulation relies upon many pulses to recruit various nerve fibers.

Stimulation of the vagus nerve is used to treat epilepsy and depression while a number of other medical conditions including eating disorders, dementia and obesity are under investigation. The human has left and right vagus nerves which descend from the base of the brain into the thorax. Current systems for stimulating the vagus nerve, so called vagal nerve stimulators, employ an electrode implanted in the cervical region of the neck. An exemplary electrode is described by Schwartz et al in U.S. Pat. No. 3,421,511 herein, incorporated in its entirety, by reference. The electrode is connected to a lead, an insulated conductor that extends between the electrode and an implanted pulse generator. An exemplary electrical stimulator for the vagus nerve is described by Zabara in U.S. Pat. No. 5,025,807 herein, incorporated in its entirety, by reference. For controlling or preventing epileptic seizures, the pulse generator generates electrical pulses having a frequency of between 30 and 300 cycles per second (Herz), a pulse duration of between 0.3 and 1 millisecond and a constant current of between 1 and 20 milliamperes. The generator is implanted in the body. Electrode leads pass from the generator through a subcutaneous tunnel and terminate in an electrode patch on the vagus nerve.

When stimulating the vagus nerve, the recurrent laryngeal nerve may also be stimulated as it is part of the vagus nerve. Some applications take advantage of this effect such as that described by Goldfarb in U.S. Pat. No. 5,111,814, incorporated herein in its entirety, by reference. However, for medical applications where laryngeal stimulation is unintended, it may have an undesired effect. As described by Baker in U.S. Pat. No. 5,205,285, incorporated herein in its entirety by reference, stimulation of the vagus nerve can cause undesirable modulation of the voice. The effect on the voice can include alteration of the voice, coughing and hoarseness. While reducing the strength of the stimulation may alleviate the undesired effect, the beneficial medical effect may also be lost. To achieve therapeutic efficacy, sufficient stimulation strength must be delivered. Unfortunately, the undesired effects of laryngeal stimulation can reduce the amount of stimulation which can be tolerated by the patient.

Baker (U.S. Pat. No. 5,205,285) discloses an apparatus to suppress the stimulation while the patient is speaking including a speech sensor and discriminator. The Baker apparatus provides selective suppression of the stimulation while the patient is speaking. The suppression of nerve stimulation is ceased after a preset time interval regardless of continued detection of speech.

Ben Ezra et al, in US pub. No. 2005/0065553 A1 and incorporated herein in its entirety, by reference, describes applications of vagal stimulation in which stimulation parameters are varied with detected phases of respiration.

If the adverse effects of the vagus nerve stimulation are avoided, a higher output of the implantable stimulator device might be tolerated by the patient and the therapeutic effect increased. Without an apparatus to mitigate the adverse effects of vagus nerve stimulation the stimulator output strength may be limited by the adverse effect to the level that the patent can tolerate.

SUMMARY OF THE INVENTION

Achieving vagus nerve stimulation output in sufficient strength to accomplish therapeutic goals for the patient is frequently compromised by patient tolerance, especially the nuisance of unintentional laryngeal stimulation. Higher outputs can be tolerated by patients if the stimulation is restricted to periods when the patient is not speaking. Speaking occurs during the exhalation or expiration phase of the patient's respiration. This application discloses an apparatus and methods for reducing the stimulation strength during the exhalation, or expiration, phase of the patient's respiration.

During inhalation, the stimulation parameters may be set at normal strength, which in many cases will be the maximum strength the patient can tolerate, as discussed above. During exhalation, the stimulation parameters may be adjusted to deliver a reduced stimulation strength. In many cases, this reduced strength will be the maximum stimulation strength possible in without adverse effects on speech

DETAILED DESCRIPTION OF THE INVENTION

Figure 1:
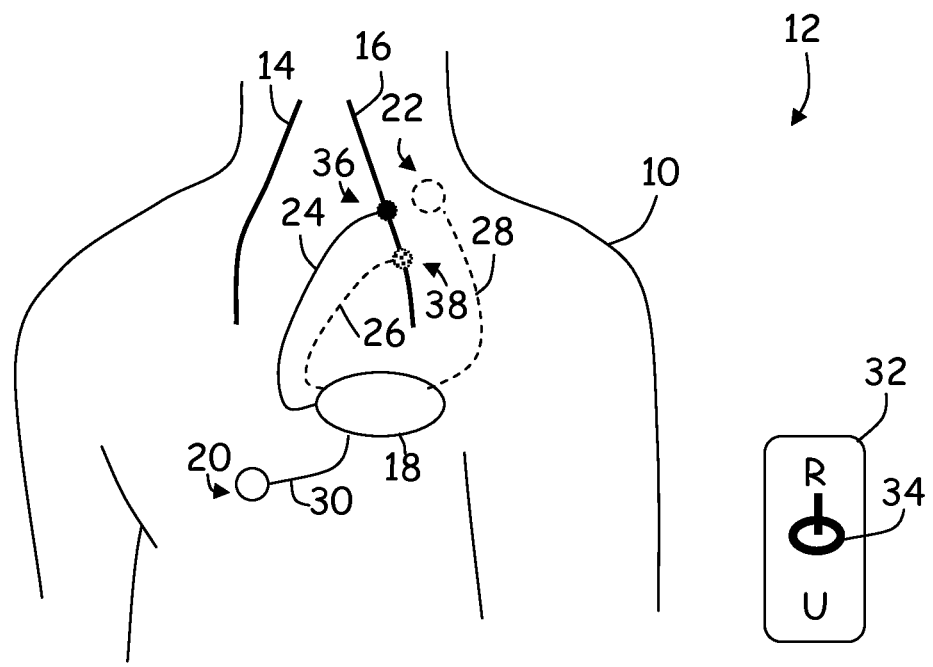
FIG. 1 is a schematic illustration of a patient, a stimulator, a respiration sensor and a patient control unit.

FIG. 1 illustrates patient 10 with a vagal nerve stimulation system 12. Right vagus nerve 14 and left vagus nerve 16 are shown descending from the base of the brain and into the thorax of patient 10. Implantable stimulator 18 is connected via lead 24 to electrode 36 on left vagus nerve 16. Respiration sensor 20 is connected to implantable stimulator 18 via lead 30. Lead 26, electrode 38, optional speech sensor 22 and lead 28 are utilized in alternative embodiments as described below. Patient control unit 32 incorporates switch 34. Switch 34 may be toggled by patient 10 or other user (not shown) to one of two positions, respiration responsive mode R and respiration unresponsive mode U.

Figure 2:
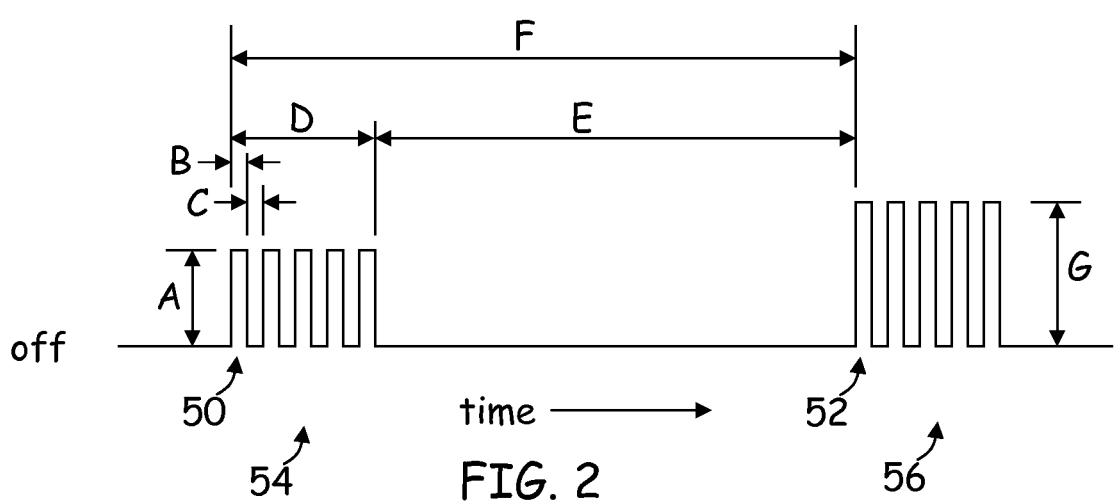
FIG. 2 is a timing diagram of two exemplary bursts of pulses. Stimulation strength of the pulses is greater for the second burst as compared to the first burst.
Figure 4:
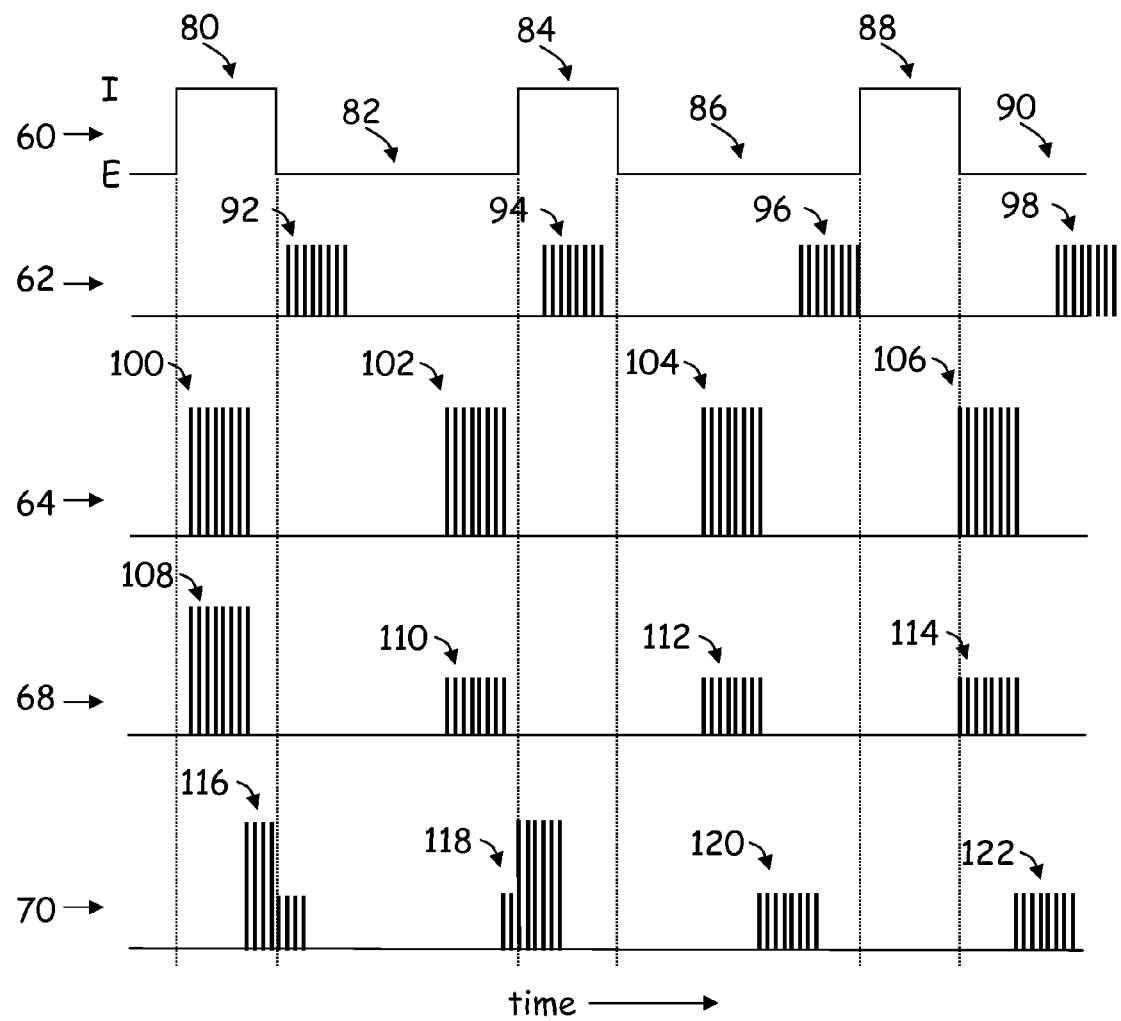
FIG. 4 is a block diagram of an exemplary pulse generator.

Stimulator 18 emits electrical pulses as shown in the timing diagram of FIG. 2 with bursts 54, 56. First burst 54 begins with pulse 50 and incorporates pulses of strength A. Each pulse lasts for duration B followed by period C, intervening time period between pulses during which stimulation is not generated. First burst 54 is of burst period D. In the example illustrated in FIG. 2 and solely for illustrative purposes, burst period D contains 5 pulses. After rest period E, second burst 56 is issued beginning with pulse 52. Second burst 56 incorporates pulses of strength G where strength G is greater than strength A. Pulses may be of different strength, both between bursts as illustrated in FIG. 2 and within a burst as illustrated in FIG. 4 and described below.

During burst 54, the stimulation is on for duration B during each of the 5 pulses and the stimulation is off for duration C for the 4 intervening intervals of the 5 pulses. During burst 54, the stimulation is on for 5×B over burst period D. The proportion of time during burst 54 that the stimulation is on is: (5×B)/D.

FIG. 2 illustrates the generation of bursts of pulses for a burst period followed by a rest period in which no pulses are generated. A burst period is followed by a rest period which, in turn is followed by a burst period, in a repetitive cycle. Burst 56 incorporates pulses during burst period D followed by rest period E; the stimulation is on for period D and off for period E. Cycle length F is the sum of burst period D and rest period E. As illustrated, stimulation pulses in burst 56 are delivered at a lesser strength than in burst 54.

Respiration sensor 20 is coupled with stimulator 18 via lead 30. Stimulator 18 via respiration sensor 20 detects the inspiration and the expiration phases of the patient's respiration, for example using the techniques disclosed in U.S. Pat. No. 6,641,542 by Cho et al., incorporated in its entirety herein by reference. Respiration sensor 20 may comprise at least one of the following: an impedance sensor and a body movement sensor. Respiration of patient 10 is detected as the inspiration phase and the expiration phase as illustrated in top panel 60 of FIG. 4 and described below.

Figure 3:
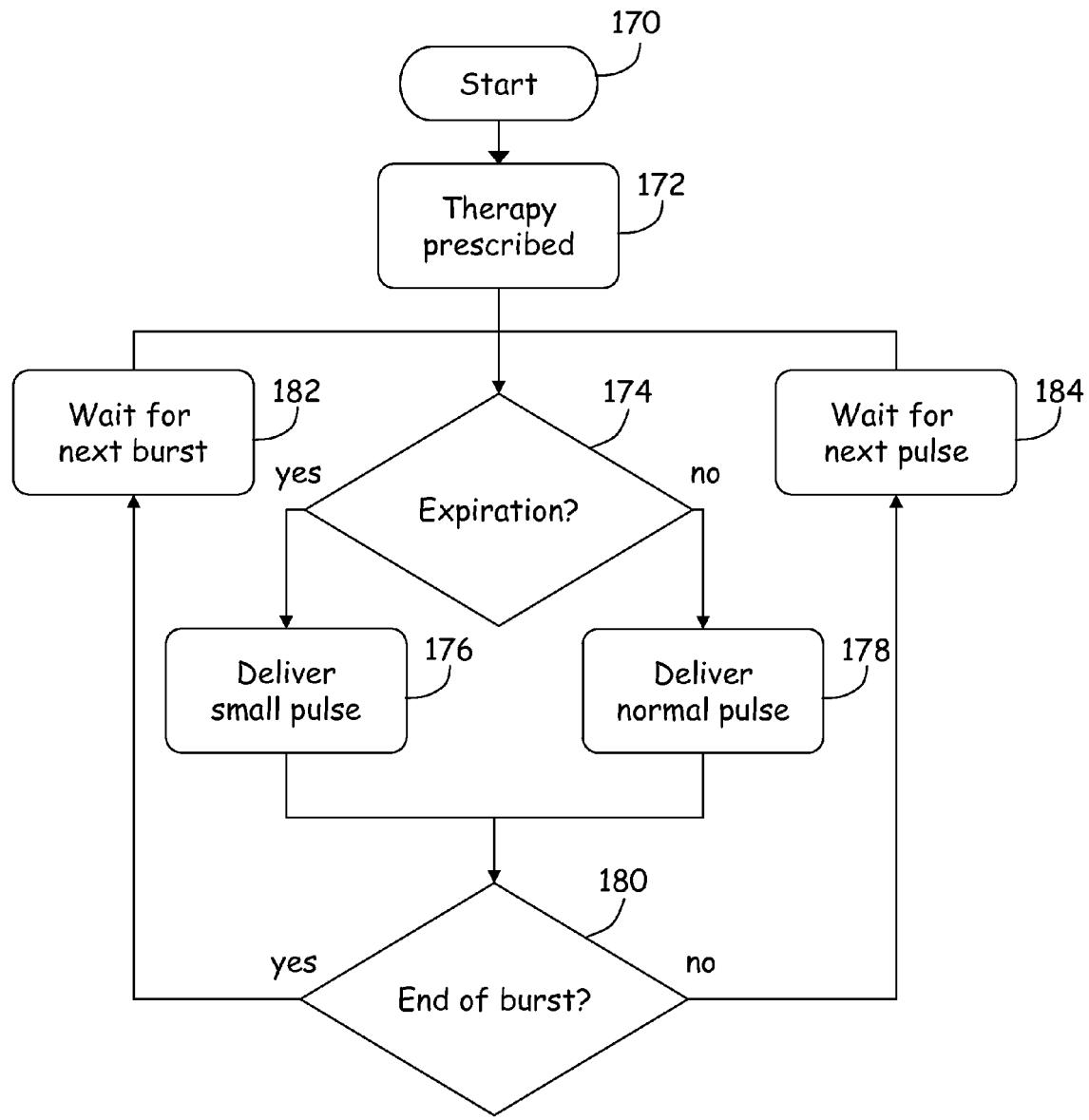
FIG. 3 is a timing diagram of the inspiration and expiration phases of the respiration of a patient and four panels of pulse bursts in time alignment with the respiration of the patient.

FIG. 3 illustrates a process to change an output parameter of vagal nerve stimulator 18 starting with step 170. Proceeding to step 172, a physician or a user (not shown) prescribes a therapy for patient 10 by establishing stimulation parameters including the strength of a normal pulse and a small pulse. In step 174 a check of respiration sensor 20 is made to determine whether the respiration of patient 10 is in the expiration phase. If "no", the respiration phase is not the expiration phase, the process continues in step 178 where stimulator 18 delivers a pulse as prescribed by the physician (described above). If "yes", the respiration is the expiration phase and in step 176 stimulator 18 delivers a reduced strength pulse. From steps 176, 178, the process continues to step 180 where stimulator 18 determines whether to end delivery of reduced strength pulses.

In some embodiments, delivery of reduced strength pulses may end in response to a defined number of pulses being delivered. This number may be the same or different from the number of pulses of pulse bursts comprising pulses of normal, relatively greater pulse strength. In other embodiments, delivery of reduced strength pulses may be ended responsive to the cumulative stimulation energy delivered during the pulse burst equaling that delivered during a pulse burst of normal strength pulses If "yes", the process continues in step 182 where rest period E (FIG. 1) is timed before returning to step 174. If "no", the process continues in step 184 where stimulator 18 intervening period C (FIG. 1) is timed before returning to step 174. Thus, for each pulse, the patient's respiration is checked to determine whether it is in the expiration phase or the inspiration phase. If the patient's respiration is determined to be in the expiration phase, stimulator 18 emits a pulse of less strength; if the patient's respiration is determined to be in the inspiration phase, stimulator 18 emits a normal pulse, a pulse of normal strength. In some embodiments, the pulse generator may optionally be coupled to a first portion of the vagus nerve during the inspiration phase and to a second portion of the vagus nerve during the expiration phase by means of included switching circuitry.

In some embodiments, the transition between pulses of greater and lesser strength within a pulse burst may be gradual, occurring over a series of pulses. In other embodiments, the entire transition may occur between two pulses When stimulator 18 via respiration sensor 20 detects an inspiration phase of the patient's respiration, the output parameters of the pulses are adjusted to provide a relatively lesser stimulation strength; when an expiration phase of the patient's respiration is detected, the output parameters are set at a greater strength, which in many cases will be the greatest available pulse strength the patient can tolerate. The parameter or parameters adjusted may include one or more of an amplitude, a voltage, a current, a proportion of time stimulating during a burst, a burst period, a ratio of the burst period to the rest period, and a number of pulses in the burst period.

Stimulator 18 generates bursts of pulses asynchronous to the respiration of patient 10. As patient 10 breathes, some bursts and some pulses will occur during an inspiration phase of the patient and some will occur during an expiration phase of the patient. The nature of this interaction implies that the application of stimulation for the vagus nerve will at some times occur when a patient exhales and the strength of the stimuli may be reduced. FIG. 4 illustrates the respiration of patient 10 in top panel 60. Legend I, on the left, refers to the inspiration phase of the respiration and legend E, also on the left, refers to the expiration phase of the respiration. Expiration phases 60, 82, 86 90 and inspiration phases 80, 84, 88 are illustrated in top panel 60.

Panel 62 illustrates bursts 92, 94, 96, 98; each occurs during the expiration phase of the respiration; each pulse of each burst is reduced strength. Panel 64 illustrates bursts 100, 102, 104, 106; each occurs during the inspiration phase of the respiration; each pulse of each burst is delivered at the normal, greater strength. Panel 68 illustrates bursts 108, 110, 112, 114; burst 108 occurs during the inspiration phase of the respiration; each pulse of burst 108 is normal strength; bursts 110, 112, 114 occur during the expiration phase of the respiration; each pulse of bursts 110, 112, 114 are delivered at a reduced strength.

Panel 70 illustrates bursts 116, 118, 120, 122; burst 116 begins during the inspiration phase of the respiration and ends during the expiration phase of the respiration; corresponding to the phase of the respiration, the first pulses in burst 116 are at normal strength and the last pulses in burst 116 are of lesser strength. In a complementary fashion, burst 118 begins during the expiration phase and completes in the inspiration phase of the respiration. The first pulses of burst 118 are small and the last pulses are of normal strength. Bursts 120, 122 both occur in the expiration phase of the respiration; each of the pulses in bursts 120, 122 are of reduced strength.

Figure 5:
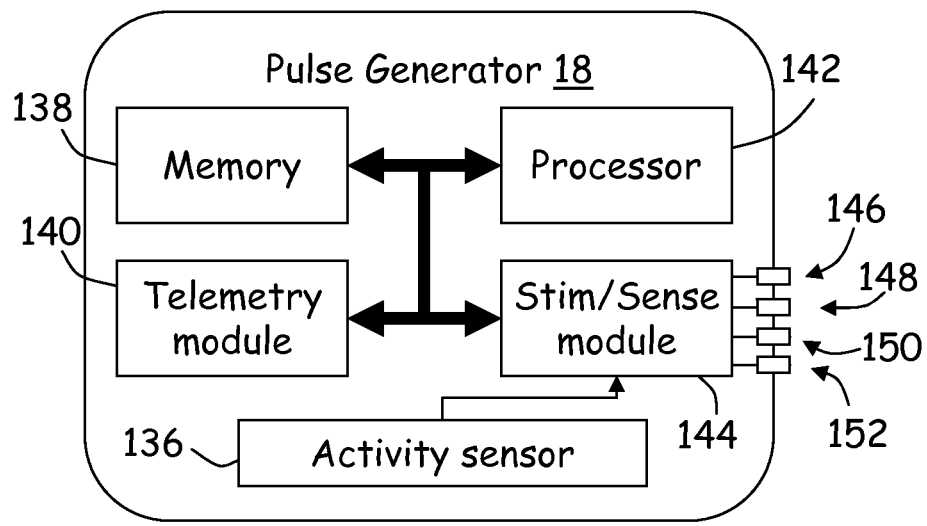
FIG. 5 is a block diagram of an exemplary patient control unit.

An exemplary pulse generator 18 block diagram is shown in FIG. 5. The pulse generator comprises memory 138, telemetry module 140, processor 142 and stimulation/sensing module 144. Stimulation output 146 is coupled to electrode 36 via lead 24 (shown in FIG. 1). Stimulation output 148 is coupled to electrode 38 via lead 26 (described below). Input 150 is coupled to respiration sensor 20 via lead 30. Input 152 is optionally coupled to a speech sensor 22 via lead 28 (FIG. 1). Activity sensor 136 is coupled to stimulation/sensing module 144. Memory 138, telemetry module 140, processor 142 and stimulation/sensing module 144 communicate with each other via a data bus, as illustrated.

The memory 138 contains stored programming which comprises an instruction set for controlling operation of the device. FIG. 3, discussed above is exemplary of such an instruction set generally. The instruction set is executed by the processor 142, which in turn controls generation of pulses by stim/sense module 144, including control of pulse parameters and pulse timing as discussed above. Processor 142 is also responsive to signals received from the various sensors within and coupled to the pulse generator and employs these signal, according to the stored instruction set, to regulate delivery of stimulation pulses.

Figure 6:
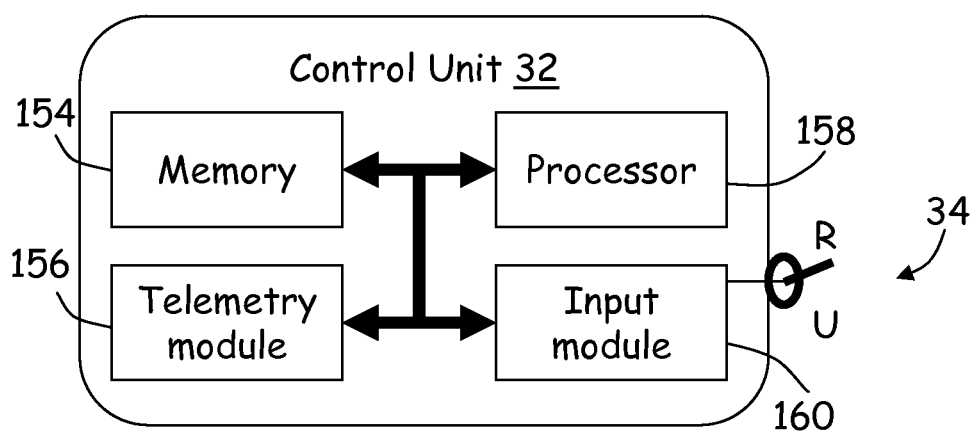
FIG. 6 is a flow diagram of a process to deliver a burst of pulses responsive to the respiration of the patient.

Patient control unit 32 block diagram is shown in FIG. 6 incorporating memory 154, telemetry module 156, processor 158 and input module 160. Switch 34 on patient control unit 32 shown in position R can be toggled to respiration responsive mode R and respiration unresponsive mode U. Memory 154, telemetry module 156, processor 158 and input module 160 communicate with each other via a data bus, as illustrated. Patient control unit 32 communicates with pulse generator 32 via wireless telemetry module 156 and corresponding telemetry module 140 in pulse generator 18. When switch 34 is toggled to a new position, control unit 32 sends the position of the switch to pulse generator 18. In respiration mode, the adjustable output parameter or parameters from pulse generator 18 are, as discussed above, different during the inspiration and expiration phases of the respiration; in respiration unresponsive mode, the output parameter from pulse generator 18 is not different during the inspiration and expiration phases of the respiration.

In another embodiment, the processor 142 determines whether patient 10 is asleep via activity sensor 136 by detecting periods of prolonged inactivity. There is little chance the patient will need to speak when asleep and the patient can likely tolerate a higher stimulation output when asleep. When the processor 142 determines patient 10 is asleep, the pulse generator adjustable output parameter or parameters may be set to provide a greater stimulation strength during the expiration phase of the respiration than when the patient is not asleep. Alternatively, the pulse generator may be set to operate in respiration unresponsive mode during sleep.

In some embodiments, the patient may not receive sufficient cumulative therapy levels for the intended medical benefit if the planned stimulation is often reduced because it occurs during the expiration phase of the respiration. In some such embodiments, parameters of delivered stimulation pulses may be stored in memory 138 over a period of time ranging from 1 to 24 hours. The processor 142 may employ its stored information to recognize when the cumulative delivered stimulation is less than the planned or desired cumulative stimulation level.

Processor 142 may accommodate for the interruptions by providing an increased stimulation strength at other times such as when the patient is sleeping (sleep sensor described above), when the patient is inhaling (respiration sensor described above), when the patient is not talking (speech sensor described below), or when the patient directs the stimulator with the patient control unit (described above) as the patient recognizes he/she will not be meeting with others and will not need to speak. To answer the telephone, make a telephone call or speak to someone, patient 10 can interrupt this period of stronger stimulation by use of patient control 32 to return the stimulator 18 to the respiration responsive mode R.

In some such embodiments, processor 142 18 may alternatively recognize cumulative the inadequacy of the stimulation by means of an included PID controller, utilized to regulate a cumulative delivered stimulation parameter such as: the number of coulombs delivered, the energy delivered and the number of pulses times the voltage. The charge, the number of coulombs, delivered may be measured by stimulator 18 by measuring the current during periods of stimulation. The energy delivered may be measured by measuring the current delivered (described above), the voltage of each pulse, and the time duration of each pulse. A less computationally demanding method may simply require the measurement of the voltage of each pulse. Processor 142 may accumulate this data in memory 138 for use by the PID controller.

In another embodiment and with reference to FIG. 1, stimulator 18 directs the stimulation output to electrode 38 via lead 26 during the expiration phase of the respiration. By directing the stimulation to electrode 38 during expiration and to electrode 36 during inspiration, a different part of the vagus nerve. Refer to FIG. 1 and the alternative lead and electrode.

In conjunction with the above description, I claim:

1. A system for stimulating a vagus nerve of a patient comprising:
    a pulse generator having an adjustable pulse output parameter and adapted to be electrically coupled to the vagus nerve,
    wherein the pulse generator generates pulses for a burst period that is followed by a rest period,
    wherein the pulse generator does not generate pulses for the rest period that is followed by the burst period;
    a respiration sensor coupled to the pulse generator,
    wherein, the respiration sensor detects the inspiration and the expiration phases of the respiration; and
    the pulse generator generates stimulation pulses during both the detected inspiration and expiration phases and wherein the pulses are delivered with the output parameter adjusted to provide greater stimulation strength during the inspiration phase than during the expiration phase.

2. The system of claim 1, wherein the adjustable output parameter is one of an amplitude, a voltage, a current, a proportion of time stimulating during a burst, a burst period, a ratio of the burst period to the rest period, and a number of pulses in the burst period.

3. The system of claim 1, wherein the adjustable output parameter regulates to one of: the number of coulombs delivered, the energy delivered, and the number of pulses times the voltage.

4. The system of claim 1, further comprising means for determining cumulative stimulation delivered over a period of 1 to 24 hours and for adjusting the output parameter to provide pulses of increased strength in response thereto.

5. The system of claim 1 wherein the pulse generator is adapted to be coupled to a first portion of the vagus nerve during the inspiration phase and to a second portion of the vagus nerve during the expiration phase by means of included switching circuitry.

6. The system of claim 1, further comprising a sleep sensor coupled to the pulse generator, wherein the sleep sensor detects whether the patient is asleep.

7. The system of claim 6, wherein the adjustable output parameter during the expiration phase is greater responsive to the sleep sensor detecting that the patient is asleep than responsive to the sleep sensor detecting that the patient is not asleep.

8. The system of claim 1, further comprising a speech sensor coupled to the pulse generator, wherein the speech sensor detects whether the patient is speaking.

9. The system of claim 8, wherein, the adjustable output parameter is greater responsive to the speech sensor indicating that the patient is not speaking as compared to when the speech sensor indicates the patient is speaking.

10. The system of claim 1, further comprising a patient control unit coupled to the pulse generator, wherein the control unit is responsive to a user input and the control unit offers the user a selection of a respiration responsive mode or a respiration unresponsive mode.

11. The system of claim 10, wherein the adjustable output parameter is the same during the inspiration and the expiration phases, when the user selects the respiration unresponsive mode; and the pulse generator output parameter is different during the inspiration and expiration phases, when the patient selects the respiration responsive mode using the patient control unit.

* * * * *